United States Patent [19]
Enomoto

[11] Patent Number: 5,311,224
[45] Date of Patent: May 10, 1994

[54] OPTICAL OPHTHALMIC TREATMENT APPARATUS

[75] Inventor: Masanori Enomoto, Nishio, Japan

[73] Assignee: Nidek Co., Ltd., Aichi, Japan

[21] Appl. No.: 951,127

[22] Filed: Sep. 25, 1992

[30] Foreign Application Priority Data

Oct. 4, 1991 [JP] Japan .................. 3-285586

[51] Int. Cl.⁵ .............................. A61B 3/10
[52] U.S. Cl. .................... 351/214; 351/221; 606/4
[58] Field of Search .............. 351/214, 221; 606/4, 606/6, 13, 14

[56] References Cited

U.S. PATENT DOCUMENTS

| | | | |
|---|---|---|---|
| 3,096,767 | 7/1963 | Gresser et al. | 351/221 |
| 4,409,979 | 10/1983 | Roussel et al. | 606/4 |
| 4,517,980 | 5/1985 | Tagnon | 606/4 |
| 4,582,405 | 4/1986 | Muller et al. | 351/221 |
| 4,732,460 | 3/1988 | Kele et al. | 606/4 |
| 4,736,744 | 4/1988 | Koike et al. | 606/4 |
| 4,830,483 | 5/1989 | Kohayakawa et al. | 606/4 |
| 4,901,718 | 2/1990 | Bille et al. | 606/4 |
| 5,067,951 | 11/1991 | Greve | 351/221 |
| 5,125,922 | 6/1992 | Dwyer et al. | 606/14 |
| 5,226,903 | 7/1993 | Mizuno | 606/4 |

FOREIGN PATENT DOCUMENTS

| | | | |
|---|---|---|---|
| 4135187 | 4/1992 | Fed. Rep. of Germany | 351/221 |
| 267847 | 5/1989 | German Democratic Rep. | 606/4 |
| 64-58255 | 3/1989 | Japan. | |
| 698191 | 3/1986 | U.S.S.R. | 606/4 |
| 85/1870 | 5/1985 | World Int. Prop. O. | 606/4 |

OTHER PUBLICATIONS

"Nanolas TM 15", Product Brochure, biophysic médical s.s., France; 1988.

Primary Examiner—Richard A. Bertsch
Assistant Examiner—Howard R. Richman
Attorney, Agent, or Firm—Finnegan, Henderson, Farabow, Garrett & Dunner

[57] ABSTRACT

An optical ophthalmic treatment apparatus comprises: a slit illuminating light beam projecting optical system having a reflecting member for reflecting a narrow illuminating light beam toward a patient's eye to illuminate the patient's eye; a stereomicroscopic observation optical system for observing the patient's eye; a first therapeutic light beam projecting optical system for introducing a first therapeutic light beam through a position on the side of an operator with respect to the reflecting member into the stereomicroscopic observation optical system; a light path deflecting optical element capable of being inserted in and retracted from a plane including the light paths of the stereomicroscopic observation optical system, of transmitting at least part of the narrow illuminating light beam and of reflecting a second therapeutic light beam; and a second therapeutic light beam projecting optical system for projecting the second therapeutic light beam which is reflected toward the patient's eye by the light path deflecting optical element inserted in the stereomicroscopic observation optical system. Thus, the optical ophthalmic treatment apparatus is capable of satisfactorily and selectively using different therapeutic light beams and has a simple construction.

15 Claims, 4 Drawing Sheets

OPTICAL OPHTHALMIC TREATMENT APPARATUS

BACKGROUND OF THE INVENTION

1. Field of the Invention

The present invention relates to an optical ophthalmic treatment apparatus and, more specifically, to an optical ophthalmic treatment apparatus capable of selectively projecting an incisive YAG (yttrium-aluminum-garnet) laser beam to be used principally for the treatment of the front portion of the eye or a coagulative semiconductor laser beam to be used principally for the treatment of the fundus of the eye.

2. Description of the Prior Art

A known optical ophthalmic treatment apparatus irradiates the affected part of the eye with a therapeutic light beam, while the operator observes the eye illuminated by a slit lamp through a stereomicroscopic observation optical system. Some optical ophthalmic treatment apparatus uses an incisive YAG laser beam principally for the treatment of the front portion of the eye and other optical ophthalmic treatment apparatus uses a coagulative laser beam, such as argon laser beam or a semiconductor laser beam, principally for the treatment of the fundus.

FIG. 4 shows a previously proposed optical ophthalmic treatment apparatus capable of selectively using an incisive laser beam or a coagulative laser beam. As shown in FIG. 4, a YAG laser beam Ly and an argon laser beam La are guided, respectively, by separate half mirrors 52 and 53 to the light path of an observation optical system. When using the argon laser beam La, an illuminating light beam Ls is guided to the light path of the observation optical system and the components of the illuminating optical system including prisms are arranged on the side of the operator's eye E with respect to an objective lens 54 to avoid the interference of the components of the illuminating optical system with the argon laser beam La. Thus, the argon laser beam, i.e., a coagulative laser beam, is transmitted through the slit lamp optical system and the YAG laser beam, i.e., an incisive laser beam, is transmitted through the observation optical system. In FIG. 4, indicated at Lh is a collimating He—Ne laser beam projected together with the YAG laser beam Ly.

FIG. 5 shows another previously proposed optical ophthalmic treatment apparatus. As shown in FIG. 5, an incisive YAG laser beam Ly projected by a YAG laser 70 is expanded by a beam expanding concave lens 71, the expanded YAG laser beam Ly is reflected by the reflecting surface 67b of a laser beam reflecting prism 67 and collimated by a relay lens 68, the collimated YAG laser beam Ly is reflected by the reflecting surface of a laser beam reflecting mirror 62 so as to travel along the light path of an observation optical system, and then the YAG laser beam Ly is focused on an affected part of the patient's eye E. An illuminating prism 72 for reflecting an illuminating light beam Ls emitted by a slit lamp toward the patient's eye E is shifted to a position where the illuminating prism 72 will not obstruct the YAG laser beam Ly. A collimating He-Ne laser beam Lh for collimating the YAG laser beam Ly relative to the affected part is emitted by a He—Ne laser, not shown, and the He—Ne laser beam Lh is transmitted through an optical fiber cable 69 to the reflecting surface 67a of a laser beam reflecting prism 67. Then, the He—Ne laser beam Lh is reflected by the reflecting surface 67a so as to travel in parallel to the light path of the YAG laser beam Ly. A coagulative argon laser beam La emitted by an argon laser, not shown, is transmitted through an optical fiber cable 63, condensed by a lens 64, reflected by a movable mirror 65, condensed further and focused on the laser beam reflecting prism 67 by a lens 66 and travels along the light path of the He—Ne laser beam Lh.

In these two prior art optical ophthalmic treatment apparatus, the argon laser beam and the YAG laser beam travel along the same light path into the observation optical system at a position on the side of the operator with respect to the slit reflecting prism and the objective lens of the observation optical system.

In the former prior art optical ophthalmic treatment apparatus, which transmits the coagulative laser beam through the slit lamp optical system, the optical system for the coagulative laser beam turns together with the slit lamp optical system, which makes the observation of the illuminated part difficult.

In the latter prior art optical ophthalmic treatment apparatus needs a complex optical system for coaxially guiding the laser beam and the illuminating light differing from each other in wavelength. Furthermore, since the therapeutic laser beam is introduced into the observation optical system into the observation optical system through a position on the side of the operator with respect to the slit reflecting prism, the slit reflecting prism must be located outside the light path of the illuminating light.

SUMMARY OF THE INVENTION

The present invention has been made in view of the foregoing disadvantages of the prior art and it is therefore an object of the present invention to provide an optical ophthalmic treatment apparatus of a simple construction, capable of properly and selectively using different therapeutic light beams, such as an incisive YAG laser beam to be used principally for treating the front part of the eye and a coagulative semiconductor laser beam to be used principally for treating the fundus.

In one aspect of the present invention, an optical ophthalmic treatment apparatus comprising a slit lamp illuminating optical system for projecting a narrow light beam through a reflecting member on the patient's eye, and a binocular observation optical system for the observation of the patient's eye is provided with a first irradiating system for guiding a first therapeutic light beam via a position on the side of the operator with respect to the reflecting member, a light path deflecting optical element capable of being inserted in and retracted from a plane including the light path of the binocular observation optical system at a position on the side of the patient's eye with respect to the reflecting member, of transmitting at least part of the illuminating light emitted by the slit lamp and of reflecting a second therapeutic light beam, and a second irradiating optical system for guiding the second therapeutic light beam reflected by the light path deflecting optical element inserted in the light path of the binocular observation optical system toward the patient's eye.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENT

Figure 1:
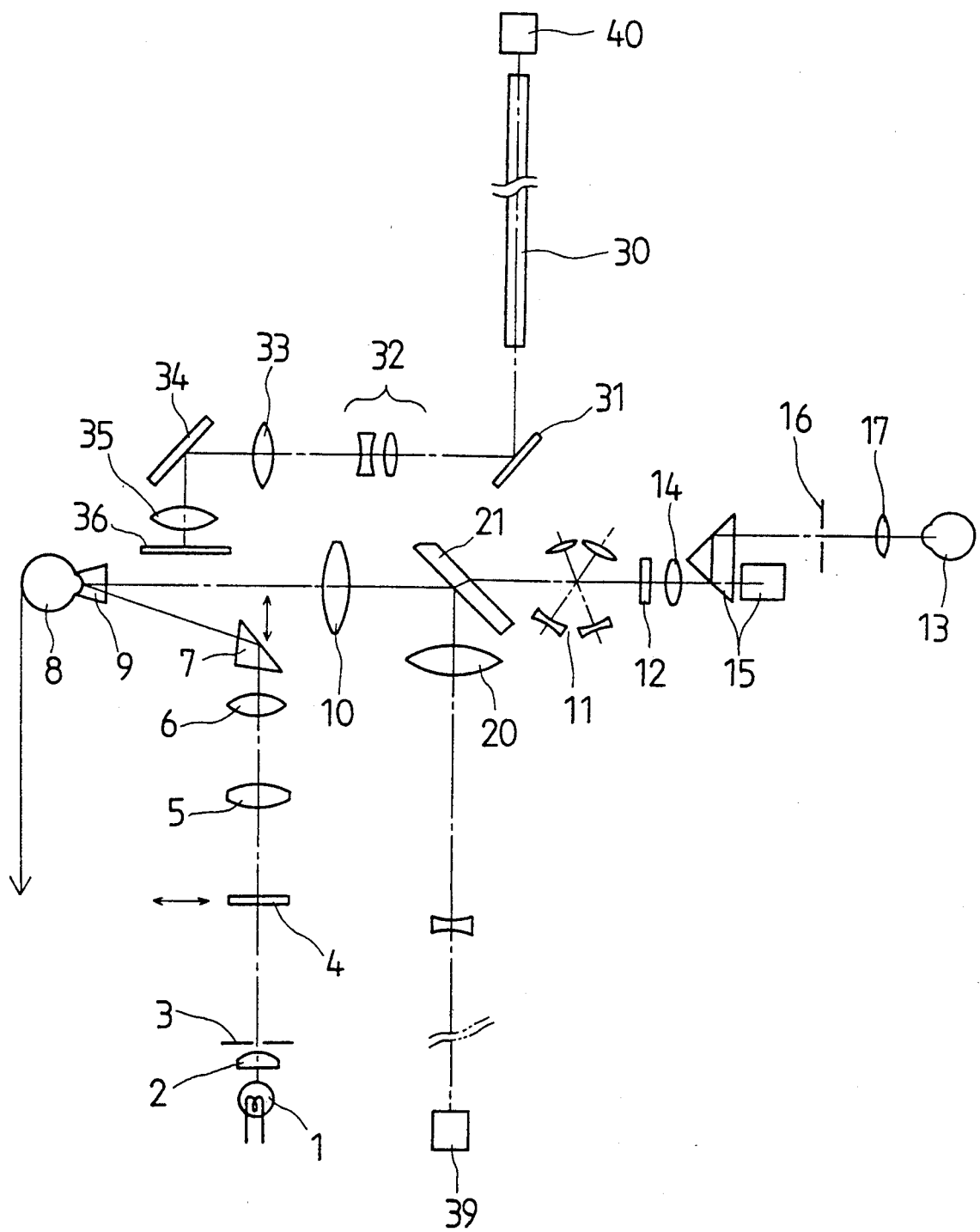
FIG. 1 is a diagrammatic view of an optical ophthalmic treatment apparatus in a preferred embodiment according to the present invention.

Referring to FIG. 1, an optical ophthalmic treatment apparatus in a preferred embodiment according to the present invention comprises a stereomicroscopic observation optical system, a slit beam projection optical system, a YAG laser beam projecting optical system and a semiconductor laser beam projecting optical system.

Slit Beam Projection Optical System

Figure 2:
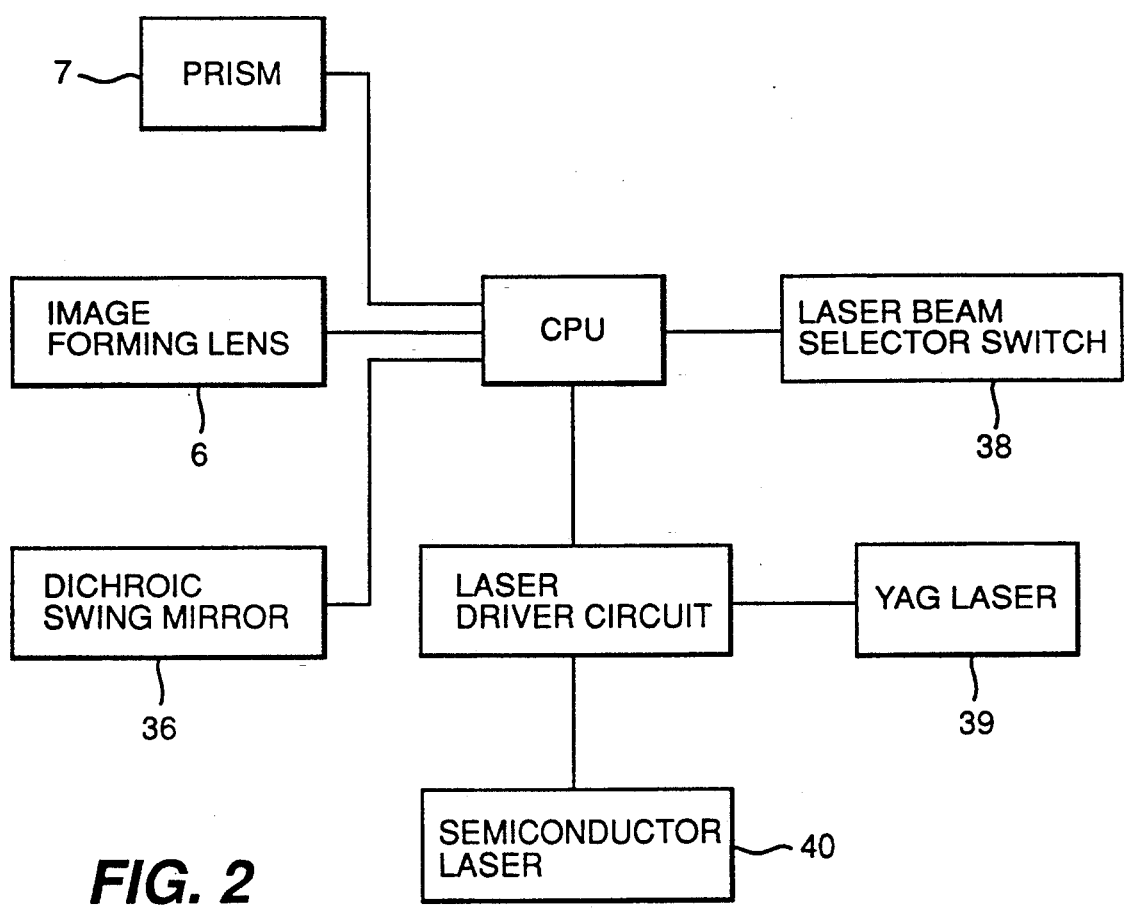
FIG. 2 is a block diagram of an essential portion of the optical ophthalmic treatment apparatus of FIG. 1.
Figure 3:
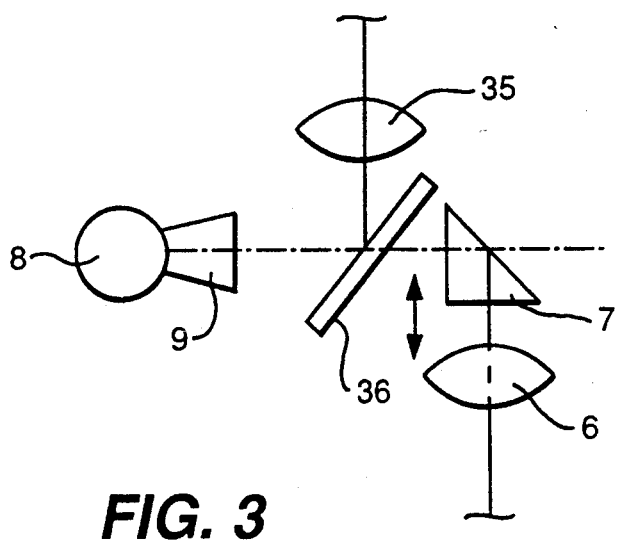
FIG. 3 is a diagrammatic view of an optical system of the optical ophthalmic treatment apparatus of FIG. 1 in a state where a semiconductor laser beam is used.
Figure 4:
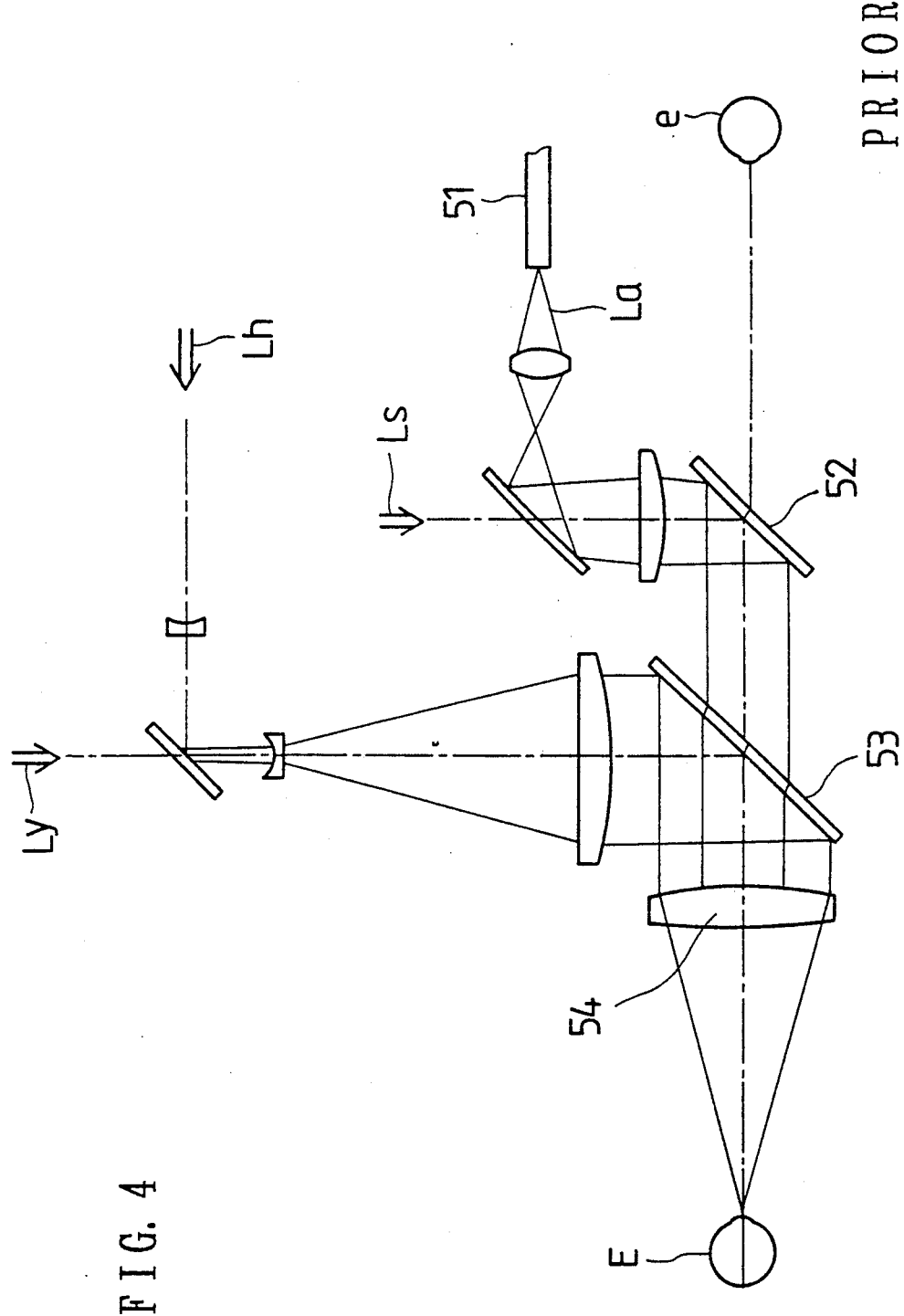
FIG. 4 is a diagrammatic view of the optical system of a prior art optical ophthalmic treatment apparatus.
Figure 5:
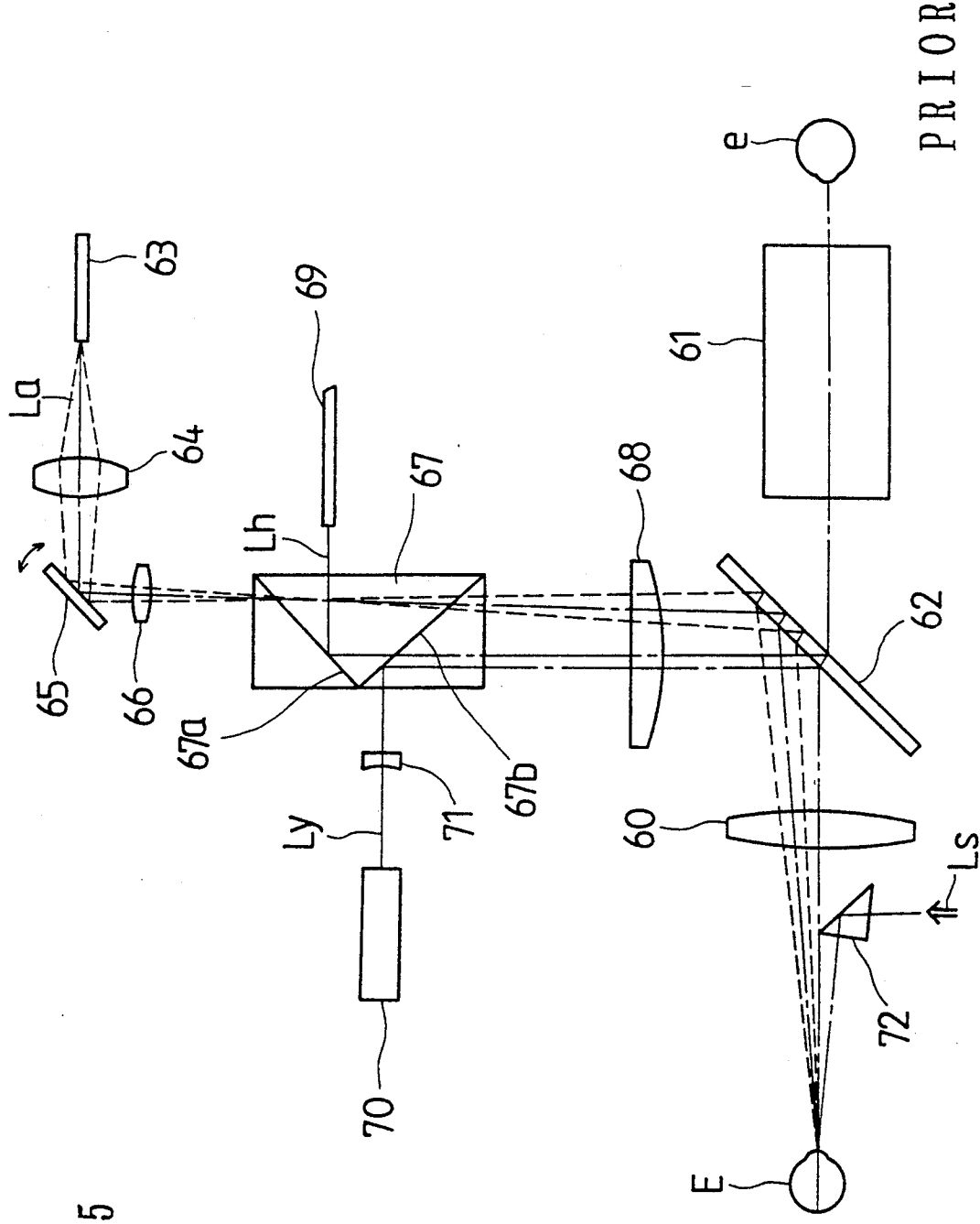
FIG. 5 is a diagrammatic view of the optical system of another prior art optical ophthalmic treatment apparatus.

The slit beam projection optical system comprises a lamp 1, a condenser lens 2 for condensing a light beam emitted by the lamp 1, a slit plate 3 having a slit through which the condensed light beam travels, a filter unit 4 having a plurality of filters which are disposed on the light path one at a time, a slit beam projecting lens 5 for collimating the light beam traveled through the filter of the filter unit 4, an image forming lens 6, and a prism 7 for reflecting the light beam toward a patient's eye 8. Normally, the filter unit 4 is held outside the light path. The light beam reflected by the prism 7 illuminates the patient's eye 8 through a contact lens 9 fitted over the cornea of the patient's eye 8. The prism 7 is moved away from the light path when a YAG laser beam is selected by operating a laser beam selector switch 38 (FIG. 2). The prism 7 is disposed on the light path with the center of the reflecting surface thereof positioned at the middle between the right and left observation optical axes and, at the same time, the image forming lens 6 is shifted along the optical axis thereof to correct the change of the optical path length when a semiconductor laser beam is selected by operating the laser beam selector switch 38 as shown in FIG. 3. A mechanism comprising, in combination, a cylindrical cam mechanism and a cam for tilting an optical element and shifting other lens along its optical axis simultaneously with the movement of the optical element along its optical axis is a known mechanism, and hence the description thereof will be omitted. The operation of the prism 7 and the image forming lens 6 is controlled by a microcomputer. The prism 7 may be shifted manually between the operating position and the standby position. The slit beam projection optical system can be turned about a vertical axis V to connect the slit beam projection optical system with the light path of the stereomicroscopic observation optical system or to disconnect the same from the light path of the stereomicroscopic observation optical system.

Stereomicroscopic Observation Optical System

The stereomicroscopic observation optical system consists of two identical optical units each comprising an objective lens 10, a variable power mechanism 11 comprising Galilean variable power lenses, a protective filter 12 for protecting operator's eyes 13 from the therapeutic laser beam, a relay lens 14, a Porro prism 15, a field stop 16 and an ocular 17.

YAG Laser Beam Projecting Optical System

The YAG laser beam projecting optical system comprises a YAG laser 39, a condenser lens 20 and a dichroic mirror 21. A YAG laser beam emitted by the YAG laser 39 through a light quantity regulating member travels coaxially with a He—Ne laser beam for collimation. The YAG laser beam is expanded and collimated by the condenser lens 20. The collimated YAG laser beam is reflected by the dichroic mirror 21 so as to travel along the optical axis of the stereomicroscopic observation optical system. Then, the YAG laser beam falls through the objective lens 10 on the patient's eye 8.

Semiconductor Laser Beam Projecting Optical System

The semiconductor laser beam projecting optical system comprises a semiconductor laser 40, an optical fiber cable 30 for transmitting a semiconductor laser beam emitted by the semiconductor laser 40, a reflecting mirror 31, a spot size variator 32, a projection lens 33 for collimating the semiconductor laser beam, a reflecting mirror 34, an image forming lens 35 and a dichroic swing mirror 36 that reflects part of a He—Ne laser beam, reflects a semiconductor laser beam of 800 nm in wavelength and transmits most part of the light emitted by the lamp 1. The dichroic mirror 36 is inserted in the stereomicroscopic observation optical system when the semiconductor laser beam is selected by operating the laser beam selector switch 38, and removed from the stereomicroscopic observation optical system when the YAG laser beam is selected by operating the laser beam selector switch 38. The dichroic mirror 36 may be shifted manually by operating a knob.

The operation of the optical ophthalmic treatment apparatus thus constructed will be described hereinafter. After completing preparatory work, such as work for fitting an appropriate contact lens over the cornea of the patient's eye 8, the position of the apparatus is adjusted relative to the patient's eye 8, and then, the patient is made to direct the line of vision toward a fixation lamp, not shown.

Then, the laser beam selector switch 38 is operated to select either the YAG laser beam or the semiconductor laser beam according to the purpose of the ophthalmic treatment. When the YAG laser beam is selected, the microcomputer controls motors to retract the prism 7 from the light path of the YAG laser beam and to move the image forming lens 6 for optical path length adjustment.

Then, the lamp 1 of the slit beam projection optical system is lighted up to project a light beam from behind the slit plate 3. The light beam emitted by the lamp 1 is collimated by the slit projection lens 5. The collimated light beam travels through the image forming lens 6 and is reflected by the prism 7 toward the patient's eye 8. Then, the light beam falls through the contact lens 9 on the patient's eye 8 to illuminate the patient's eye 8. Observing the patient's eye 8 by means of the stereomicroscopic observation optical system, the operator operates a joystick, not shown, or turns the slit beam projection optical system about the vertical axis V so that an affected part of the patient's eye 8 requiring ophthalmic treatment is illuminated properly.

After collimating the stereomicroscopic observation optical system on the affected part of the patient's eye 8 by using the He—Ne laser beam, the push button of an irradiation switch is pushed to irradiate the affected part of the patient's eye 8 with the YAG laser beam.

If the affected part is on the fundus, the semiconductor laser beam is used. When the laser beam selector switch 38 is operated to select the semiconductor laser beam, the microcomputer controls the motors to locate the prism 7 with the center of its reflecting surface at the middle between the respective optical axes of the right and left optical units of the stereomicroscopic observation optical system as shown in FIG. 3 and to shift the condenser lens 6 accordingly. Then, the fundus is irradiated with the semiconductor laser beam after collimation.

The present invention is not limited to the foregoing embodiment in its practical application and many changes and variations are possible therein. For example, laser beams other than the YAG laser beam and the semiconductor laser beams may be used.

What is claimed is:

1. An optical ophthalmic treatment apparatus comprising:
   a slit beam projection optical system for projecting a narrow illuminating light beam, having a reflecting member for reflecting the narrow illuminating light beam toward a patient's eye to illuminate the patient's eye said reflecting member having at least a side of an operator and a side of the patient's eye;
   a stereomicroscopic observation optical system for observing the patient's eye;
   a first therapeutic light projecting optical system for projecting a first therapeutic light beam so that the first therapeutic light beam is introduced into the stereomicroscopic observation optical system though a position on the side of an operator with respect to the reflecting member;
   a light path deflecting optical element capable of being inserted in and retracted from a plane including light paths of the stereomicroscopic observation optical system through a position on the side of the patient's eye with respect to the reflecting member, capable of transmitting at least part of the light beam projected by the slit beam projection optical system and capable of reflecting a second therapeutic light beam; and
   a second therapeutic light projecting optical system for projecting the second therapeutic light beam so that the second therapeutic light beam is reflected by the light path deflecting optical element inserted in the light path of the stereomicroscopic observation optical system toward the patient's eye.

2. An optical ophthalmic treatment apparatus according to claim 1, wherein said light path deflecting optical element deflects the second therapeutic light beam when retracted from the plane including the light paths of the stereomicroscopic observation optical system.

3. An optical ophthalmic treatment apparatus according to claim 1, wherein said light path deflecting optical element is a dichroic mirror.

4. An optical ophthalmic treatment apparatus according to claim 1, wherein said reflecting member can be moved away from a light path along which the first therapeutic light beam travels.

5. An optical ophthalmic treatment apparatus according to claim 4, wherein said reflecting member reflects the narrow illuminating light beam toward the patient's eye from a position outside a light path along which the first therapeutic light beam travels when the first therapeutic light beam is projected on the patient's eye and reflects the narrow illuminating light beam toward the patient's eye from a position on the light path along which the first therapeutic light beam travels when the second therapeutic light beam is projected on the patient's eye.

6. An optical ophthalmic treatment apparatus comprising:
   a slit beam projection optical system for projecting a narrow illuminating light beam, having a reflecting member for reflecting the narrow illuminating light beam toward a patient's eye to illuminate the patient's eye;
   an observation optical system for observing the patient's eye;
   a first therapeutic light beam projecting optical system having a first light path deflecting optical element disposed in the observation optical system to introduce a first therapeutic light beam into the observation optical system so that the first therapeutic light beam travels along a light path of the observation optical system to the patient's eye; and
   a second therapeutic light beam projecting optical system having a second light path deflecting optical element capable of being inserted in and retracted from the observation optical system and of introducing a second therapeutic light beam into the observation optical system so that the second therapeutic light beam travels along the light path of the observation optical system to the patient's eye.

7. An optical ophthalmic treatment apparatus according to claim 6, wherein said first therapeutic light beam is an incisive laser beam to be used principally for treatment of the front part of the patient's eye, and said second therapeutic light beam is a coagulative laser beam to be used principally for the treatment of the fundus of the patient's eye.

8. An optical ophthalmic treatment apparatus according to claim 7, wherein said incisive laser beam is a YAG (yttrium-aluminum-garnet) laser beam, and said coagulative laser beam is a semiconductor laser beam.

9. An optical ophthalmic treatment apparatus according to claim 6, wherein said reflecting member is a prism.

10. An optical ophthalmic treatment apparatus according to claim 9, wherein said prism can be inserted in and retracted from a light path of said observation optical system.

11. An optical ophthalmic treatment apparatus according to claim 10, further comprising:
    a therapeutic light beam selector switch means for selecting either the first therapeutic light beam or the second therapeutic light beam; and
    a prism shifting and controlling means for moving said prism away from the light path of said observation optical system when the first therapeutic light beam is selected by operating the therapeutic light beam selector switch means and inserting said prism in the light path of said observation optical system when the second therapeutic light beam is selected by operating the therapeutic light beam selector switch means.

12. An optical ophthalmic treatment apparatus according to claim 11, further comprising a light path deflecting optical element driving and controlling means for moving said second light path deflecting optical element away from the light path of said observation optical system when said therapeutic light beam selector switching means is operated to select the first therapeutic light beam.

13. An optical ophthalmic treatment apparatus according to claim 6, wherein said first light path deflecting optical element is a dichroic mirror capable of transmitting the narrow illuminating light beam and of reflecting the first therapeutic light beam.

14. An optical ophthalmic treatment apparatus according to claim 6, wherein said second light path deflecting optical element is a dichroic mirror capable of transmitting the narrow illuminating light beam and of reflecting the second therapeutic light beam.

15. An optical ophthalmic treatment apparatus according to claim 6, wherein said slit beam projection optical system is capable of being turned about an optical axis thereof.

* * * * *